United States Patent [19]

Mildenberger et al.

[11] Patent Number: 5,153,355
[45] Date of Patent: Oct. 6, 1992

[54] PROCESS FOR THE EXTRACTIVE SEPARATION OF L-PHOSPHINOTHRICIN AND L-GLUTAMIC ACID IN AQUEOUS SOLUTION

[75] Inventors: Hilmar Mildenberger, Kelkheim/Taunus; Harald Knorr, Frankfurt am Main; Arno Schulz, Eppstein/Taunus; Heribert Tetzlaff, Frankfurt am Main, all of Fed. Rep. of Germany

[73] Assignee: Hoechst Aktiengesellschaft, Frankfurt am Main, Fed. Rep. of Germany

[21] Appl. No.: 748,268

[22] Filed: Aug. 21, 1991

[30] Foreign Application Priority Data

Aug. 23, 1990 [DE] Fed. Rep. of Germany ....... 4026628

[51] Int. Cl.⁵ .................. C07C 227/00; C07C 229/08
[52] U.S. Cl. ..................................... 562/11; 562/554
[58] Field of Search .................. 562/11, 554

[56] References Cited

U.S. PATENT DOCUMENTS 4,536,596  8/1985  Savides et al. .

FOREIGN PATENT DOCUMENTS 0166992  6/1985  European Pat. Off. .
0247436  5/1987  European Pat. Off. .

OTHER PUBLICATIONS

Per-Ake Albertsson, Nature, vol. 177, (1956), S. 771 ff.

Primary Examiner—Jose G. Dees
Assistant Examiner—Joseph M. Conrad, III
Attorney, Agent, or Firm—Curtis, Morris & Safford

[57] ABSTRACT

A large number of customary processes for separating amino acids fails when very polar hydrophilic amino acids with isoelectric points (IEP) which are close to one another are to be fractionated. Mixtures of L-glutamic acid (IEP=3.24) and L-phosphinothricin (IEP=2.6) produced by enzymatic transaminations of the corresponding α-keto acid have been difficult to separate to date. The invention relates to a process for separating L-phosphinothricin and L-glutamic acid, which comprises carrying out the separation as liquid-/liquid extraction with two non-miscible aqueous phases as phase system, where the phase former contained in the phase system is a combination of at least two different water-soluble polymers or of at least one water-soluble salt and one water-soluble polymer, and the extraction is carried out by multistage countercurrent partition on the van Dijck principle.

18 Claims, No Drawings

PROCESS FOR THE EXTRACTIVE SEPARATION OF L-PHOSPHINOTHRICIN AND L-GLUTAMIC ACID IN AQUEOUS SOLUTION

Description

Various processes are used to separate amino acids. These include, for example, electrodialysis, (ion exchange) chromatography, extraction and crystallization processes. However, a large number of these processes fails or is associated with considerable disadvantages when very polar hydrophilic amino acids with isoelectric points (IEP) which are close to one another are to be fractionated. The mixture of L-glutamic acid (IEP =3.24) and L-phosphinothricin (IEP =2.6) represents such a combination. Mixtures of this type are produced, for example, in the preparation of L-phosphinothricin (L-PTC, i.e. L-2-amino-4-(hydroxymethylphosphinyl)-butanoic acid) by enzymatic transamination of α-keto acid (i.e. 4-(hydroxymethylphosphinyl)-2-oxobutanoic acid) in the presence of an excess of L-glutamic acid (see, for example, EP-A-248357).

The partition behavior of the two amino acids on liquid/liquid extraction (i.e. on partition thereof between two non-miscible phases) is determined by their partition coefficients which are defined as the ratio of the amino acid concentration in one phase to the concentration in the other phase. The quotient of the partition coefficients of the two amino acids is called the separation factor and is a measure of the complexity of separation (number of stages, ratio of phase quantities) necessary in countercurrent partition in order to separate the two amino acids from one another to a particular extent. As the separation factor increases, the theoretical number of stages required decreases. extraction processes in which it is possible, with the aid of water-insoluble phase-transfer catalysts (liquid ion exchangers) such as quaternary nitrogen, sulfur, phosphorus or boron bases, or else with water-insoluble sulfonic acids, to remove the amino acids lysine, phenylalanine, tryptophan and glutamic acid from aqueous solution. In principle, L-PTC can also be extracted with these extractants from aqueous solution, but the partition coefficients for the two polar hydrophilic amino acids glutamic acid and L-PTC in the relevant two-phase systems are each only in the narrow range from 0.1 to 0.2. It is therefore impossible to separate them from one another economically by the stated methods (see comparative examples below).

DE-A-1277256 describes a process in which amino acids are extracted with the aid of dinonylnaphthalenesulfonic acid or the sodium salt thereof as cation exchanger and dichloromethane from aqueous solution of pH 2–5. However, the extractability of L-PTC and L-glutamic acid is too low for a process to be used economically because the amounts of extraction phase required are too high. In addition, the working up of the extracts by the displacement extraction with organic amines described therein is too laborious.

U.S. Pat. No. 4,536,596 describes a process of extraction of amino acids which contain only one carboxyl group from aqueous solution with the aid of dithiophosphinates. However, the process is unsuitable for the extraction of L-glutamic acid (see U.S. Pat. No. 4,536,596, column 7, Tab. III) and thus also for the extraction of L-PTC which is even more hydrophilic.

JP-14444/68 describes a process in which amino acids such as, inter alia, glutamic acid can be extracted with tri(lower alkyl) phosphates from aqueous solution. However, the efficiency of the method is insufficient to separate L-glutamic acid and L-PTC (see comparative examples below).

In DE-A-2822870, amino acids are extracted from aqueous solution with a mixture of an aliphatic $C_4$–$C_8$-ketone and partially neutralized cumenesulfonic acid. It is necessary for the amino acids to be in the acidic bisulfate form for this. In this process, a large number of process steps are necessary and a large amount of salts is produced as waste, so that the process is less suitable for industrial use.

EPA-0251852 describes a process in which amino acids can be extracted from aqueous solution with the aid of dialkyl/aryl phosphoric acids, phosphonic acids or phosphinic acids. However, L-glutamic acid is not sufficiently extractable with organophosphorus acids (see comparative examples below).

Because of the abovementioned disadvantages, none of the processes mentioned is suitable for efficient separation of L-glutamic acid and L-PTC from aqueous solution.

The invention relates to a process for separating L-phosphinothricin and L-glutamic acid, which comprises carrying out the separation as liquid/liquid extraction with two non-miscible aqueous phases as phase system, where the phase former contained in the phase system is a combination of at least two different water-soluble polymers or of at least one water-soluble salt and one water-soluble polymer, and the extraction is carried out by multistage countercurrent partition on the van Dijck principle.

The phase systems composed of non-miscible aqueous phases which can be used for the process according to the invention have been known in principle for a long time (see, for example, P.-A. Albertsson, Nature, Vol. 177, 771 (1956) and P.-A. Albertsson in "Partition of Cell Particles and Macromolecules", 2nd Edition/3rd Edition, John Wiley & Sons, New York 1971 and 1986). They are produced, for example, by mixing two different water-soluble polymers, or one polymer and one salt, with an aqueous phase. It was hitherto known that, on partition of substances between two aqueous phases of this type, partition coefficients above 100 can be achieved only for large molecules (for example DNA), and up to 10 can be achieved for smaller molecules such as proteins and enzymes, whereas small molecules and salts usually partition approximately equally (see, for example, P.-A. Albertsson, Nature, Vol. 177 (1956) 773 et seq.). However, surprisingly, even for the relatively small molecules of L-glutamic acid and L-PTC there is found to be an adequate to good separation factor when said phase system composed of two non-miscible aqueous phases is employed.

Examples of suitable polymer/polymer combinations as phase former for the process according to the invention are:

a1) polyethylene glycol or polyethylene glycol monoalkyl ether or dialkyl ether in combination with polyvinyl alcohol, polyvinyl pyrrolidone, dextran or synthetic polysaccharides such as ($^R$)Ficoll weight at 400000)

a2) polyvinyl alcohol in combination with methylcellulose or dextran;

a3) polinylpyrrolidone in combination with dextran;

a4) synthetic polysaccharides such as ($^R$)Ficoll in combination with dextran.

Examples of suitable polymer/salt combinations are:

b1) polyethylene glycol or polyethylene glycol monoalkyl ether or dialkyl ether in combination with potassium sulfate, potassium phosphate or ammonium sulfate or else with sodium dextran sulfate or sodium carboxymethylcellulose;

b2) polyvinylpyrrolidone in combination with potassium phosphate;

b3) polypropylene glycol in combination with glucose;

b4) polyvinyl alcohol in combination with sodium dextran sulfate o sodium carboxymethylcellulose.

Of special interest as two-phase formers are those mentioned above in group b1). In this connection, particular attention is to be drawn to polyethylene glycol dialkyl ethers, preferably polyethylene glycol dimethyl ether with molecular weights between 250 and 2000, in particular 400 to 800, in combination with ammonium sulfate. The ammonium sulfate is preferably employed in the concentration range from 10 to 40% by weight, based on the phase containing the salt.

The ratio by weight of the two non-miscible phases is preferably 1:10 to 10:1. The separation factor depends on the pH of the phase system and is usually in the pH range from 0 to 12.5. It is preferable to work at pH 2.8 to 3.3, especially pH 3. The temperature for the process according to the invention is expediently adjusted so that a separation factor which is as good as possible is achieved, with, at the same time, good phase separation. It is usually in the range from 10 to 60° C, and preferably at room temperature.

The mixture of L-PTC and L-glutamic acid to be separated is usually introduced as aqueous solution into the two-phase system, it being possible for the aqueous solution also to contain other constituents. For example, it is possible to introduce an aqueous solution of the mixture which is to be separated such as results directly after enzymatic transamination of α-keto acid in the presence of an excess of L-glutamic acid.

The extraction scheme in the van Dijck partition is known; see, for example, O. Jübermann in Houben Weyl Vol. I/1a, G. Thieme Verlag, Stuttgart 1958, pages 249 to 255. This entails, for example, the solution of the mixture containing L-glutamic acid and L-PTC being fed into the middle of a multistage extractor partition bed composed of two non-miscible aqueous phases being passed countercurrently. The multistage procedure in the manner of the van Dijck partition results, at one end of the partition bed, in an aqueous solution which now contains virtually only L-PTC and one part of the phase-former combination, for example ammonium sulfate, while the result at the other end is an aqueous solution which now contains virtually only L-glutamic acid and the second part of the phase-former combination, for example polyethylene glycol dimethyl ether.

In a preferred embodiment of the process, for example, the aqueous solution of a mixture which contains 1 to 20% by weight, preferably 1 to 15% by weight, L-glutamic acid and 1 to 15% by weight, preferably 1 to 10% by weight, L-PTC is pumped at room temperature and pH 3 in the middle of the extraction apparatus into the partition bed composed of the two non-miscible aqueous phases. The pH of these phases has previously likewise been adjusted to 3. The system, employed to form 2 phases is polyethylene glycol dimethyl ether with a molecular weight of 500 (PEGE 500) and ammonium sulfate. The two non-miscible aqueous phases are previously generated by preparing a solution or dispersion of 21% by weight ammonium sulfate and 26% by weight PEGE 500, which spontaneously breaks up about half and half into the two aqueous phases. The amino acid mixture introduced in the middle is then subjected to multistage countercurrent partition between the two aqueous phases. The upper phase which runs out of one end of the extraction apparatus and contains the L-glutamic acid and PEGE 500 is neutralized and then distilled to remove the water, and the L-glutamic acid which is insoluble in the PEGE 500 and then precipitates out is removed by filtration. PEGE 500 is returned to the extraction (via the 2-phase formation stage). The lower phase which runs out at the other end of the apparatus is neutralized and then distilled to remove water apart from 6 to 8% by weight, and then the ammonium sulfate is precipitated by adding methanol. After removal of the salt (which is likewise recycled) by filtration, the methanol is evaporated off and the remaining melt is crystallized or adjusted to an aqueous solution of L-PTC ready for use.

Suitable apparatus for the extractive separation of L-glutamic acid and L-PTC by the van Dijck partition scheme is in principle all conventional extraction apparatus (columns, mixer settlers, Graesser extractor, centrifugal extractor), but the use of mixer settler batteries or extraction columns is preferred because of the numbers of stages required.

The process is illustrated by means of the following examples and comparative examples:

EXAMPLE 1

The following Table 1 shows the partition of L-glutamic acid and L-PTC between non-miscible aqueous phases formed from polyethylene glycol dimethyl ethers of various chain lengths and ammonium sulfate at room temperature. The dependence of, in particular, the separation factor on the pH is clear from the stated separation factors ($\beta$):

TABLE 1

|  | pH | | | | | |
|---|---|---|---|---|---|---|
|  | 0.44 | 2.07 | 3.03 | 4.02 | 8.25 | 12.35 |
| $\beta$ (PEGE 500) | 1.33 | 1.15 | 1.78 | 1.34 | 1.17 | 1.54 |
| $\beta$ (PEGE 1000) | 1.30 | 1.01 | 1.20 | 1.18 | 1.34 | 1.34 |
| $\beta$ (PEGE 2000) | 1.31 | 1.22 | 1.37 | 1.24 | 1.22 | 1.32 |

EXAMPLE 2

A transamination solution obtained by the process of EPA-248357 and adjusted to pH 3, containing 4% by weight L-glutamic acid and 1.5% by weight L-PTC, was fed at room temperature into the middle of a 20-stage laboratory mixer settler. An aqueous phase containing about 20% by weight PEGE 500 was fed in at one end of the laboratory mixer setter and an aqueous phase containing about 25% by weight ammonium sulfate was fed in at the other end. The ratio of the amounts of transamination solution to PEGE 500 phase and ammonium sulfate phase was 1:3:1. The PEGE 500 phase running out at one end of the apparatus contained about 95% pure L-glutamic acid, and the ammonium sulfate phase running out at the other end contained about 95% pure L-PTC. The glutamic acid was obtained from the PEGE 500 phase by evaporating off the water and filtering, and the mineral salt was separated out of the ammonium sulfate phase after neutralization and evaporation by addition of methanol.

EXAMPLE 3

A transamination solution containing 13.1% by weight L-glutamic acid and 3.9% by weight L-PTC and adjusted to pH 7.9 was fed at room temperature into the middle of an oscillating plate column (length 6 m, diameter 50 mm, Karr type). An aqueous phase containing about 20% by weight PEGE 500 was fed as disperse phase into the lower end of the column. An aqueous phase containing about 25% by weight ammonium sulfate was fed as continuous phase into the upper end. The transamination solution : PEGE 500 phase : ammonium sulfate phase ratio of amounts was 0.7 : 3.2 : 1.1. The PEGE 500 phase running out at the upper end of the column contained about 96% pure L-glutamic acid, and the ammonium sulfate phase running out at the lower end contained about 94% pure L-PTC. The L-glutamic acid was obtained from the PEGE 500 phase by evaporating off the water and filtering, and the mineral salt was separated out of the ammonium sulfate phase after neutralization and evaporation by addition of methanol.

COMPARATIVE EXAMPLES

Table 2 shows, by means of a comparison of the ratio of the concentration of L-glutamic acid to the concentration of L-PTC before and after the extraction, that fractionation of the two amino acids with the aid of the extractants mentioned above as state of the art is not economic because the changes in the concentration ratio, which are small at best, do not allow separation with an acceptable number of stages in a countercurrent extraction.

TABLE 2

| Extractant | L-Glu/L-PTC concentration ratio at pH | | | | |
|---|---|---|---|---|---|
| | 1.8 | 4.8 | 8.9 | 11.0 | 12.0 |
| None (initial value) | 4.5 | 4.8 | 4.9 | 4.8 | 4.8 |
| BDOPO | 4.7 | 4.9 | 4.9 | — | — |
| ® Hostarex A27 | — | 4.9 | 4.9 | — | 4.9 |
| ® Hostarex chloride | 4.7 | — | — | — | — |
| Nonylphenol | 5.2 | 4.6 | 4.7 | — | — |
| Iononanoic acid | 5.0 | 4.9 | 4.9 | — | — |
| Isobutylisooctylamine | — | 4.9 | 4.9 | — | — |
| Di-n-octylamine | — | 4.8 | 4.8 | — | — |
| ® Hostarex DK 16 | 4.9 | 4.9 | 4.9 | — | — |
| di(2-ethylhexyl) phosphate | 4.8 | — | 4.7 | 4.9 | — |
| Tributyl phosphate | — | — | 4.8 | — | 4.9 |
| Tn-OABr in ® Solvesso 100 | — | — | 4.7 | 4.9 | 4.9 |
| 50% by weight dinonyl-naphthalenesulfonic acid/kerosine | 4.8 | 4.9 | — | — | — |

Abbreviations:
BDOPO = (2-butyl)-di-(n-octyl)phosphine oxide
® Hostarex A327 = tri(n-octyl)amine:tri(n-decyl)amine (1:1)
® Hostarex DK 16 = alkylated benzoylacetone
Tn-OABr = tetra(n-octyl)ammonium bromide
® Solvesso 100 = mixture of aromatic compounds containing 80% by weight meta-$C_9$-aromatic compounds

We claim:

1. A process for separating L-phosphinothricin and L-glutamic acid, which comprises carrying out the separation as liquid/liquid extraction with two non-miscible aqueous phases as phase system, where the phase former contained in the phase system is a combination of at least two different water-soluble polymers or of at least one water-soluble salt and one water-soluble polymer, and the extraction is carried out by multistage countercurrent partition on the van Dijck principle.

2. The process as claimed in claim 1, wherein polyethylene glycol or polyethylene glycol monoalkyl ether or dialkyl ether in combination with potassium sulfate, potassium phosphate or ammonium sulfate are employed as two-phase former.

3. The process as claimed in claim 2, wherein ammonium sulfate in a concentration of 10 to 40% by weight, based on the salt-containing phase, is employed.

4. The process as claimed in claim 3, wherein polyethylenglycol dimethyl ether with molecular weights between 250 and 2000 in combination with ammonium sulfate are employed as phase former.

5. The process as claimed in claim 4, wherein the pH of the phase system is 0 to 12.5.

6. The process as claimed in claim 5, wherein the pH is 2.8 to 3.3

7. The process as claimed in claim 4, wherein the ratio by weight of the two non-miscible phases is 1:10 to 10:1.

8. The process as claimed in claim 7, wherein the separation is carried out at 10 to 60° C.

9. The process as claimed in claim 8, wherein the mixture to be separated contains 1 to 20% by weight L-glutamic acid and 1 to 15% by weight phosphinathricin.

10. The process as claimed in claim 1, wherein polyethylene glycol dimethyl ether with molecular weights between 250 and 2000 in combination with ammonium sulfate are employed as phase former.

11. The process as claimed in claim 1, wherein the pH of the phase system is 0 to 12.5.

12. The process as claimed in claim 11, wherein the ph is 2.8 to 3.3.

13. The process as claimed in claim 1, wherein the ratio by weight of the two non-miscible phases is 1:10 to 10:1.

14. The process as claimed in claim 1, wherein the separation is carried out at 10 to 60° C.

15. The process as claimed in claim 1, wherein the mixture to be separated is employed as aqueous solution as obtained after enzymatic transamination of 4-(hydroxymethylphosphinyl)-2-oxobutanoic acid in the presence of an excess of L-glutamic acid.

16. The process as claimed in claim 1, wherein the mixture to be separated contains 1 to 20% by weight L-glutamic acid and 1 to 15% by weight L-phosphinothricin.

17. The process as claimed in claim 16, wherein the mixture to be separated contains 1 to 15% by weight L-glutamic acid and 1 to 10% by weight L-phosphinothricin.

18. The process as claimed in claim 1, wherein the phases leaving the partition bed are worked up by distillation.

* * * * *